United States Patent [19]
Fuchs et al.

[11] Patent Number: 5,973,224
[45] Date of Patent: Oct. 26, 1999

[54] DIETETICAL COMBINATION PREPARATIONS

[76] Inventors: Norbert Fuchs, 135 Bruckdorf, A-5571, Mariapfarr; Norbert Zelch, 11a Wasserfeldstrasse, A-5020, Salzburg; Peter Koessler, 219 Bruckdorf, A-5571; Rupert Loidl, Tischlerhaeusl, A-5571, both of Mariapfarr, all of Austria

[21] Appl. No.: 08/648,661

[22] Filed: May 16, 1996

[30] Foreign Application Priority Data

Apr. 3, 1996 [AT] Austria ................................. A 607/96

[51] Int. Cl.⁶ ..................................................... A01C 1/00
[52] U.S. Cl. .......................... 800/200; 426/634; 426/615
[58] Field of Search ............................ 800/200; 426/634, 426/615, 531

[56] References Cited

U.S. PATENT DOCUMENTS

| | | | |
|---|---|---|---|
| 2,051,460 | 8/1936 | von Skrbensky | 47/58 |
| 3,751,261 | 8/1973 | Tatara | 99/11 |
| 4,130,964 | 12/1978 | Caballero | 47/16 |
| 4,237,651 | 12/1980 | Caballero | 47/58 |
| 4,618,454 | 10/1986 | Ballard et al. | 252/500 |

FOREIGN PATENT DOCUMENTS

| | | |
|---|---|---|
| 124 891 A2 | 11/1984 | European Pat. Off. . |
| 0 129 032 | 12/1984 | European Pat. Off. . |
| 0 616 810 | 9/1994 | European Pat. Off. . |
| 770 324 A2 | 5/1997 | European Pat. Off. . |
| 40 17 114 | 4/1991 | Germany . |
| 2100 112 | 12/1982 | United Kingdom . |

OTHER PUBLICATIONS

Harmuth–Hoene, "Dietary Fiber and the Bioavailability of Essential Trace Elements, A Controversial Topic," *In: Trace Element—Analytical Chemistry in Medicine and Biology*, vol. 4, Walter de Gruyter & Co., Berlin, New York, pp. 107–120, 1987.

Harmuth–Hoene, Bognar, Kornemann, Diehl, "The Influence of Germination on the Nutritional Value of Wheat, Mung beans and Chickpeas," *Z Lebensm Unters Forsch*, 185:386–393, 1987.

Harmuth–Hoene and Meuser, "Biologische Verfügbarkeit von Zink in Getreidevollkornprodukten mit unterschiedlichem Phytatgehalt," Z Ernährungswiss, 26:250–267, 1987.

Meier–Ploeger, "The Importance of Sprouts and Seeds Sprouts in Whole–Food Nutrition," *Nutrition*, 14(6);317–322, 1990.

Austrian Search Report Mar. 25, 1996 (SONN:003).

European Search Report Oct. 31, 1997.

Handbuch der Orthomolekularen Medizin, Dietl & Ohlenschläger, Haug publishers, 1994, (A partial translation is attached).

National Cancer Institute: Beta Carotene and Vitamin A Halted in Lung Cancer Prevention Trail, Press Information of Jan. 18, 1996.

International Search Report dated Dec. 9, 1996.

*Primary Examiner*—Ponnathapura Achutamurthy
*Assistant Examiner*—T. Wessendorf
*Attorney, Agent, or Firm*—Arnold White & Durkee

[57] ABSTRACT

The present invention relates to a combination preparation containing electrolyte-enriched plant embryos and essential, semi-essential and/or non-essential micro-nutrients, in particular for the treatment of immune-suppressed persons.

9 Claims, No Drawings

DIETETICAL COMBINATION PREPARATIONS

The invention relates to dietetical combination preparations.

The human immune metabolism is dependent on various exogenous and endogenous factors, and to a decisive extent also on the quality and quantity of the nutrients supplied.

Numerous research has documented the fact that the immune metabolism can be influenced by nutritive factors. In connection with the specific supply of individual nutrients in case of a lowered immune performance, both positive and also negative correlations have been found, in particular in connection with the supply of β-carotene and the incidence of lung cancer in smokers (National Cancer Institute: Beta Carotene and Vitamin A Halted in Lung Cancer Prevention Trial, Press information of Jan. 18, 1996).

The negative correlations to the incidence of cancer and immune diseases in those persons, who live according to the principles of health food nutrition (i.e. who consume vegetables, fruit and whole meal products regularly and largely avoid isolated or refined products) are more clearly apparent. In view of the fact that in food products on whole meal basis, nutritive substances never occur isolated, but in complex combinations of their numerous biological precursors and in the presence of numerous bioactive plant substances, which primarily do not have any nutritive functions, the biogenic nutrients must be judged completely differentiated when compared to synthetic nutrients. Thus, the stabilizing effect of health-food nutrition can be put down to the fact of the complex interaction of vitamins, their biological precursors, organically bound mineral substances and trace elements as well as bioactive plant ingredients (such as flavonoides, tannins, lignanes, phenolic acids, phytosterines, protease inhibitors etc.), i.e. substances of secondary plant metabolism.

In the course of the preliminary work carried out in connection with the present invention it has been found that the exclusive supply of health food products does not suffice to ensure a demand-covering supply of micro-nutrients in immune-suppressed persons to stabilize a derailed immune system. On the other hand, however, it has also been found that the supply of high doses of synthetic vitamin and mineral mixtures does not lead to the desired goal either, i.e. to a sufficient support of the damaged immune system.

Thus, it is the object of the present invention to provide a new nutrient mixture particularly suited to support and stabilize, respectively, the immune system, particularly a damaged or suppressed immune system.

This object of the invention is achieved by a combination preparation comprising
   electrolyte-enriched plant embryos and
   essential, semi-essential, non-essential micro-nutrients or combinations thereof.

Electrolyte-enriched plant embryos have been described in Austrian Patent Application A 1668/95, and they have an increased electrolyte content as compared to conventional plant embryos incubated in tap water. It is preferred that these electrolyte-enriched plant embryos have a content of one or several electrolytes, preferably of zinc, iron, potassium, magnesium, copper, manganese, strontium, selenium, molybdenum, chromium, arsenic, lithium, vanadium and/or cobalt ions that is increased, as compared to conventionally germinated seeds, by at least 10 to 20%, preferably by at least 1.5- to 3-fold, in particular by at least 5- to 10-fold.

It has now been shown that such electrolyte-enriched plant embryos do not only have a higher concentration of mineral substances, but are also quite generally better in terms of the substances contained therein, e.g. have a higher vitamin content, on account of their increased mineral content.

Preferably, these plant embryos are obtained by germination in an electrolyte solution of between 10 and 50° C., preferably between 20 and 30° C., for a period of time of from 12 to 240 hours, preferably of about 60 to 100 hours, the electrolyte solution containing 1 mg/l or more, preferably 10 mg/l or more, in particular 50 mg/l or more of zinc, iron, potassium and/or magnesium ions, 0.5 mg/l or more, preferably 5 mg/l or more, in particular 25 mg/l or more of copper, manganese, strontium and/or lithium ions, 0.1 mg/l or more, preferably 1 mg/l or more, in particular 5 mg/l or more of selenium, molybdenum, chromium, arsenic, vanadium and/or cobalt ions.

Plant embryos constitute a valuable enrichment of the food, particularly since they are inexpensive as compared to vegetable varieties, they are always fresh, independent of seasons, rich in dietary fibers, rich in vitamins and minerals, and in addition tasty and wholesome. Preferably, plant embryos of leguminosae and cereal seeds, such as, e.g. wheat, buckwheat, oat, quinoa, mung bean, fenugreek, radish, alfalfa, maize, squash, rye, barley, rice, adzuki bean, pea, millet, chick pea, cress, linseed, lentil, mustard, sesamum, soybean, sunflower and amaranth embryos, in particular wheat, buckwheat and oat embryos are used within the scope of the preparation according to the invention.

As mentioned before, the supply of health food products alone could not lead to a sufficient stabilization of the immune system of immune-suppressed persons. This may be caused by these patients' very individual demand of micro-nutrients, since surprisingly, the combination preparation of the present invention may cause a marked improvement of the immune metabolism.

On the other hand, the poor action of the exclusive administration of micro-nutrients to immune-suppressed persons is probably due to the absence of the secondary plant substances mentioned.

Within the scope of the invention, micro-nutrients are to be understood as substances activating metabolism (as different from energy-supplying substances) present in natural food and, simultaneously, also naturally in the human organism, and on whose sufficient supply the human body is dependent, particularly if the body is weakened by illness, stress etc., and whose supply results in a positive metabolism-activating effect on the body, such as, e.g., vitamins, minerals, trace elements, fatty acids, amino acids, enzymes and secondary (bioactive) plant ingredients (cf. "Handbuch der orthomolekularen Medizin, Dietl & Ohlenschläger (1994), Haug publishers).

Those micro-nutrients are considered as essential which are absolutely necessary for life; semi-essential micro-nutrients may optionally be replaced by other micro-nutrients or may become essential micro-nutrients under certain pathological conditions; those micro-nutrients are considered as non-essential, which are not indispensibly necessary for life (for a survival), which, however, have a positive, metabolism-activating effect when applied.

The synergetic effect obtained due to the combination of these two components according to the invention thus probably goes back to the interaction of the biogenic nutrient portions from the health food component with the micro-nutrients.

The combination preparation according to the invention optionally also contains one or several vegetable concentrates, preferably from broccoli, parsley and/or cauliflower.

In a preferred embodiment, the preparation according to the invention is composed of from 5 to 90%, preferably 20 to 70%, plant embryos, 5 to 90%, preferably 20 to 70%, micro-nutrients, and 0 to 90% other components, preferably vegetable concentrates, food-technological additives and/or auxiliary components. Food-technological additives or auxiliary components are all those additives commonly used in the production and final processing or in the making ready for selling, yet, as far as possible, here, too, care must be taken that the health food requirements from the nutritional-physiological and ecological points of view are met.

When the combination preparation according to the invention is used as a medicament, it may, of course, comprise the pharmaceutical additives, auxiliaries and active ingredients necessary or common for the respective mode of application.

According to a preferred embodiment of the present invention, the combination preparation is provided in the form of capsules, chewing tablets, powder mixtures or in particular combinations thereof and/or packed to be stable during storage in a form suitable in terms of food technology or medicament technology. When pharmaceutically using the combination preparations of the invention, the latter are preferably provided in a pharmaceutical administration form for oral use.

The combination preparations according to the invention may equally be mixed with conventional foodstuffs, which is particularly advisable with highly refined foodstuffs poor in vitamins and minerals.

The micro-nutrient component in the combination preparation according to the invention preferably is selected from the group consisting of poly-unsaturated fatty acids, preferably a PUFA-mixture of fish oil and borage oil, natural carotenoid mixtures, preferably from dunaliella salina, plant embryo extracts, preferably wheat embryo extract with octacosanole, natural anthocyano-mixtures, preferably from hibiscus blossoms, natural flavenoid mixtures, preferably from citrus fruit, tree resins and bark extracts, natural tocopherol, tocotrienol mixtures, preferably from wheat embryos, vitamins and coenzymes, preferably coenzyme Q10, pyridoxole, riboflavin, folic acid, biotin, vitamin K, vitamin B 12, vitamin D3, carnitine, betain and/or vitamin C, essential and non-essential amino acids, preferably N-acetyl cysteine, taurine, L-glutamine, isoleucine, leucine, lysine, methionine, phenyl alanine, threonine, tryptophane, valine, histidine, arginine and/or tyrosine, minerals, preferably silica earth, calcium, vanadium, manganese, iron, potassium, zinc, copper, lithium, fluorine, germanium, strontium, chromium, molybdenum, selenium and/or iodine, and other micro-nutrients, preferably quercetin, α-lipoic acid, glutathione, aneurin, inositol, orotic acid, inosine and/or p-amino benzoic acid, or mixtures thereof.

The respective concentration of the micro-nutrients may preferably be in the range of the known application instructions for these substances, it may, however, also diverge more or less from the common administration concentrations, depending on the individual requirements of the immune-suppressed persons to be treated.

It has been shown that with the following daily maximum supply dose suitable for regular administration: 78 mg β-carotene, 10 mg vitamin B1, 15 mg vitamin B2, 20 mg vitamin B6, 150 mg Niacin, 30 mg pantothenic acid, 0.02 mg B 12, 1.5 mg folic acid, 1700 mg vitamin C, 0.01 mg vitamin D3, 180 mg vitamin E, 0.04 mg vitamin K, 0.3 mg biotin, 1,400 mg potassium, 700 mg calcium, 550 mg magnesium, 29 mg iron, 34 mg zinc, 31 mg manganese, 8 mg copper, 0.3 mg selenium, 0.2 mg chromium, 0.2 mg molybdenum, 450 mg sodium, 440 mg chloride, 770 mg phosphorus, 120 mg coenzyme Q10, 350 mg α-lipoic acid, 3 mg lithium, 3 mg strontium, 136 mg flavonoides, 700 mg L-carnitine, 250 mg glutathione, very favorable, i.e. effective, results could be obtained. The daily minimum dose should be in a range lying at aproximately one third of this recommended maximum levels.

As mentioned before, an important aspect of the present invention is the prophylactic, yet in particular also the therapeutic use of the combination preparation of the invention.

It has been shown that immune-suppressed persons, in particular HIV-positive patients whose functionality of the immune system has already been impaired, can be treated efficiently with an efficient dose of the combination preparation according to the present invention, an improvement or stabilization of the immune system being obtainable by means of the combination preparation of the invention.

It has been shown that not only the concentration of the T-helper cells in the blood, or the quotient of T-helper cells and T-suppressor cells in HIV positive persons and people suffering from AIDS can be increased markedly, but that also a pathologically increased microglobulin or neopterin-level can be lowered again by using the preparation of the invention.

The effective dose applied to such patient generally is in the range as outlined above for the daily maximum supply dose but can be varied beyond this range according to the individual necessities of the patient.

The preparations according to the invention are also suitable for a number of non-medical applications, e.g. as a dietetic or a food supplement.

The invention will be explained in more detail by way of the following examples, to which, however, it shall not be limited.

EXAMPLES

A combination preparation according to the invention was administered to three pateints A, B, C over a period of from 11 to 29 months in the following daily amounts:

2.72 g of broccoli concentrate, 2.6 g of parsley concentrate, 2.68 g of cauliflower concentrate, 15 g of wheat embryos, 5 g of wheet embryo extract, 15 g of lecithine, 6.4 g of oatmeal, 5 g of dried apricots, 3 g of dried, nutrient-enriched buckwheat sprouts, 3 g of dried, nutrient enriched wheat sprouts, 3.6 g of dried, nutrient enriched oat sprouts, 6 g of dried banana fruit, 0.9 g of L-alanine, 0.7 g of L-arginine, 0.57 g of L-aspartic acid, 1 g of L glutamic acid, 2.4 g of L-glycine, 0.06 g of L-histidine, 0.12 g of L-isoleucine, 0.3 g of L-leucine, 0.38 g of L-lysine, 0.08 g of L-methionine, 0.25 g of L-phenyl alanine, 0.12 g of L-proline, 0.28 g of L-serine, 0.15 g of L-threonine, 0.05 g of L-tyrosine, 0.25 g of L-valine, 0.006 g of L-cystine, 1 g of potassium, 500 mg of magnesium, 500 mg of sodium, 0.2 mg of molybdenum, 0.5 mg of biotine, 3 mg of lithium, 3 mg of copper, 10 mg of zinc, 50 mg of inosine, 50 mg or para-aminobenzoic acid, 5 mg of germanium, 10 mg of manganese, 50 mg of betaine, 100 mg of coenzyme Q10, 100 mg of taurine, 40 mg of EPA, 500 mg of N-acetyl-cysteine, 330 mg of bioflavonoides, 330 mg of anthocyanes, 150 mg of GLA, 100 mg of L-glutamine, 0.01 mg of vitamin D3, 0.01 mg of vitamin B12, 0.07 mg of vitamin K, 0.2 mg of iodide, 1.8 mg of fluoride, 0.2 mg of selenium, 0.75 mg of folic acid, 0.2 mg of chromium, 3 mg of strontium, 15 mg of pantothenic acid, 25 mg of vitamin B2, 0.4 mg of vanadium, 25 mg of vitamin B1, 2 mg of octacosanol, 50 mg of niacine, 250 mg of reduced glutathione, 50 mg of vitamin B6, 50 mg of orotic acid, 10 mg of iron, 124 mg of calcium, 200 mg of silicon, 50 mg β-carotene. During this time, a large number of parameters was examined in these patients on a regular basis.

Patient A

During the period from the 1st examination to the 4th examination, patient A ate a health food diet, yet without any micro-nutrient supplementation; during the period between the 4th and 5th examinations, the patient ate the combination preparation of the invention, i.e. health food supplemented by micro-nutrients; during the period between the 5th and 7th examinations, the patient finally ate health food, but again did not take any additional micro-nutrients. The results of the examinations in respect of T-helper and T-suppressor cells and their ratios, respectively, are summarized in Table 1.

All the data examined appear from Table 2.

TABLE 1

| Patient A HIV-pos., male | 1st Exam. | 4th Exam. 9 months | 5th Exam. 12 months | 7th Exam. 24 months |
| --- | --- | --- | --- | --- |
| T-helper | 540 | 250 | 710 | 392 |
| T-suppressor | 690 | 360 | 770 | 685 |
| Ratio | 0.78 | 0.69 | 0.92 | 0.57 |

TABLE 2

| Patient A | 1st Exam. | 2nd Exam. | 3rd Exam. | 4th Exam. | 5th Exam. | 6th Exam. | 7th Exam. | 8th Exam. | 9th Exam. | 10th Exam. | 11th Exam. | 12th Exam. | 13th Exam. |
|---|---|---|---|---|---|---|---|---|---|---|---|---|---|
| Duration | 0 Months | 4 Months | 6 Months | 9 Months | 12 Months | 16 Months | 24 Months | 29 Months | | | | | |
| T-Suppressor (250–1000/mcl) | 690 | 680 | 1080 | 360 | 770 | 570 | 685 | 765 | | | | | |
| T-Suppressor % (19–48%) | 47.00% | 51.00% | 57.00% | 51.00% | 46.00% | 45.00% | 56.00% | 51.00% | | | | | |
| T-Helper abs. (500–1500/mcl) | 540 | 450 | 570 | 250 | 710 | 500 | 392 | 555 | | | | | |
| T-Helper % (29–59%) | 37.00% | 34.00% | 30.00% | 35.00% | 42.00% | 40.00% | 32.00% | 37.00% | | | | | |
| Quotient (0,9–2,0) | 0.78 | 0.66 | 0.53 | 0.69 | 0.92 | 0.88 | 0.57 | 0.73 | | | | | |
| Activated T-C. abs. | 380 | | | 100 | 240 | | | | | | | | |
| Activated T-C. % (2–12%) | 26.00% | | | 14.00% | 14.00% | | | | | | | | |
| aktiv. Suppressor abs. (CD8/HLA-DR) | | | | | | 210 | 379 | 330 | | | | | |
| aktiv. Suppr. % (2–12%) (CD8/HLA-D | | | | | | 17.00% | 31.00% | 22.00% | | | | | |
| CD38 aktiv. Suppr.-T. abs. | | | | | | 210 | 465 | 345 | | | | | |
| CD38 aktiv. Suppr.-T. % (5–20%) | | | | | | 17.00% | 38.00% | 23.00% | | | | | |
| NK Cells abs. (100–600/mcl) | 90 | | | 40 | 30 | 60 | 73 | 45 | | | | | |
| NK Cells % (6–29%) | 6.00% | | | 6.00% | 2.00% | 5.00% | 6.00% | 3.00% | | | | | |
| Neopterin (<200 mcmol/mol creatinine | | | | | 300 | | | | | | | | |
| Beta-Microglobulin (0,8–3,0 mg/l) | 5.18 | 3.88 | 3.71 | 2 | 1.44 | 1.4 | 2.25 | 2.7 | | | | | |
| Leucocytes abs. (4,0–10,0 G/l) | 29.90% | 32.70% | 48.80% | 3.7 | 4.3 | 4.40 | 3.6 | 5 | | | | | |
| Lymphocytes % (20–40%) | 31.00% | 2.60% | 1.90% | 0.38 | 45.00% | 32.00% | 45.00% | 31.00% | | | | | |
| Eosinophiles % (1–4%) | | | | 3.00% | 5.00% | 2.00% | 2.00% | 1.00% | | | | | |
| Total T-Cells (680–2750/mcl) | 1230 | 1140 | 1640 | 590 | 1460 | 1080 | 1053 | 1320 | | | | | |
| Total T-Cells (60–85%) | 84.00% | 86.00% | 87.00% | 84.00% | 87.00% | 86.00% | 86.00% | 88.00% | | | | | |
| Total B-Cells (71–600/mcl) | 150 | 90 | 110 | 70 | 130 | 90 | 73 | 135 | | | | | |
| Total B-Cells % (7–23%) | 10.00% | 7.00% | 6.00% | 10.00% | 8.00% | 7.00% | 6.00% | 9.00% | | | | | |
| BSG (after 1 h; 0–8 mm) | | | | | | 5 | 4 | 4 | | | | | |
| BSG (after 2 h; 0–20 mm)) | | | | | | 11 | 9 | 8 | | | | | |
| Iron (80–150 mcg/dl) | | | | | | | 138 | 148 | | | | | |
| Ferritin (29–371 ng/ml) | | | | | | | 49 | 43 | | | | | |
| Cholesterol (150–200 mg/dl) | | | | | | 167 | 179 | 165 | | | | | |
| HDL-Cholesterol (>50 mg/dl) | | | | | | 57 | 51 | 53 | | | | | |
| Triglycerides (70–150 mg/dl) | | | | | | | 72 | 50 | | | | | |
| CIC (0,0–5,9 ng/ml) | | | | | | | 1.1 | | | | | | |
| HIV 1 p24 (pg/ml) - HIV 1 EAG | | | | negative | negative | negative | negative | | | | | | |
| Hematocrit | | | | 41.00% | 41.90% | 41.20% | 42.30% | 44.00% | | | | | |

Patient B

During the period between the 1st and 4th examinations (8 months), patient B substantially ate a health food diet, with micro-nutrients additionally supplemented. The results of the T-helper/T-suppressor examinations are illustrated in Table 3 (total analysis: Table 4).

TABLE 3

| Patient B HIV-neg., female | 1st Examination | 4th Examination 20 months |
|---|---|---|
| T-helper | 550 | 789 |
| T-suppressor | 440 | 520 |
| Ratio | 1.25 | 1.52 |

TABLE 4

| Patient B | 1st Exam. | 2nd Exam. | 3rd Exam. | 4th Exam. | 5th Exam. | 6th Exam. | 7th Exam. | 8th Exam. | 9th Exam. | 10th Exam. | 11th Exam. | 12th Exam. | 13th Exam. |
|---|---|---|---|---|---|---|---|---|---|---|---|---|---|
| Duration | 0 Months | 8 Months | 15 Months | 20 Months | 28 Months | | | | | | | | |
| T-Suppressor (250–1000/mcl) | 440 | 880 | 590 | 520 | 486 | | | | | | | | |
| T-Suppressor % (19–48%) | 30.00% | 34.00% | 33.00% | 29.00% | 30.00% | | | | | | | | |
| T-Helper abs. (500–1500/mcl) | 550 | 1170 | 780 | 789 | 745 | | | | | | | | |
| T-Helper % (29–59%) | 38.00% | 45.00% | 44.00% | 44.00% | 46.00% | | | | | | | | |
| Quotient (0,9–2,0) | 1.25 | 1.33 | 1.32 | 1.52 | 1.53 | | | | | | | | |
| Activated T-C. abs. | 60 | 50 | | | | | | | | | | | |
| Activated T-C. % (2–12%) | 4.00% | 2.00% | | | | | | | | | | | |
| aktiv. Suppressor abs. (CD8/HLA-DR) | | | 50 | 36 | 32 | | | | | | | | |
| aktiv. Suppr. % (2–12%) (CD8/HLA-D | | | 3.00% | 2.00% | 2.00% | | | | | | | | |
| CD38 aktiv. Suppr.-T. abs. | | | | | 178 | | | | | | | | |
| CD38 aktiv. Suppr.-T. % (5–20%) | | | | | 11.00% | | | | | | | | |
| NK Cells abs. (100–600/mcl) | 160 | 260 | 210 | 161 | 146 | | | | | | | | |
| NK Cells % (6–29%) | 11.00% | 10.00% | 12.00% | 9.00% | 9.00% | | | | | | | | |
| Neopterin (<200 mcmol/mol creatinine | | | | | 1.3 | | | | | | | | |
| Beta-Microglobulin (0,8–3,0 mg/l) | 5.6 | 7 | 7.1 | 6.9 | 5.6 | | | | | | | | |
| Leucocytes abs. (4,0–10,0 G/l) | 30.00% | 42.00% | 26.00% | 30.00% | 32.00% | | | | | | | | |
| Lymphocytes % (20–40%) | 1.00% | 3.00% | 3.00% | 1.00% | 2.00% | | | | | | | | |
| Eosinophiles % (1–4%) | 930 | 1940 | 1250 | 1220 | 1053 | | | | | | | | |
| Total T-Cells (680–2750/mcl) | 64.00% | 75.00% | 70.00% | 68.00% | 65.00% | | | | | | | | |
| Total T-Cells % (60–85%) | 290 | 390 | 340 | 305 | 324 | | | | | | | | |
| Total B-Cells (71–600/mcl) | 20.00% | 15.00% | 19.00% | 17.00% | 20.00% | | | | | | | | |
| Total B-Cells % (7–23%) | | | | | 13 | | | | | | | | |
| BSG (after 1 h; 0–8 mm) | | | | | 30 | | | | | | | | |
| BSG (after 2 h; 0–20 mm) | | | | | 61 | | | | | | | | |
| Iron (80–150 mcg/dl) | | | | | 7 | | | | | | | | |
| Ferritin (29–371 ng/ml) | | | 204 | | 185 | | | | | | | | |
| Cholesterol (150–200 mg/dl) | | | 69 | | 62 | | | | | | | | |
| HDL-Cholesterol (>50 mg/dl) | | | 117 | | 57 | | | | | | | | |
| Triglycerides (70–150 mg/dl) | | | | | 1.7 | | | | | | | | |
| CIC (0,0–5,9 ng/ml) | | | | | | | | | | | | | |
| HIV 1 p24 (pg/ml) - HIV 1 EAG | | | | | | | | | | | | | |
| Hematocrit | 34.10% | 35.50% | 38.50% | 38.30% | 37.40% | | | | | | | | |

Patient C

During the period between the 1st and 3rd examinations, patient ate a health food diet, with micro-nutrients supplemented; between the 3rd and 4th examinations, patient C ate a health food diet and supplemented micro-nutrients in combination with health food concentrates. The results in respect of T-helper and T-suppressor cells are illustrated in Table 5 (total analysis: Table 6).

TABLE 5

| Patient C HIV pos., female | 1st Exam. | 3rd Exam. 7 months | 4th Exam. 11 months |
|---|---|---|---|
| T-helper | 574 | 465 | 577 |
| T-suppressor | 714 | 509 | 507 |
| Ratio | 0.80 | 0.91 | 1.14 |

The increase or decrease, respectively, of T-helper cells, and the course of the ratio T-helper to T-suppressor cells are viewed as important laboratory parameters in judging the status of the immune system of immune-suppressed patients, in particular of HIV-positive patients. As illustrated by a comparison of the T-helper/T-suppressor cell levels, and also of the remaining values of the three patients listed shows that a stabilization of the immune functions can be achieved the most effectively by a combined supply of standardized micro-nutrient amounts on the basis of highly valuable health food concentrates, as they can be provided by the combination preparation according to the invention.

TABLE 6

| Patient C | 1st Exam. | 2nd Exam. | 3rd Exam. | 4th Exam. | 5th Exam. | 6th Exam. | 7th Exam. | 8th Exam. | 9th Exam. | 10th Exam. | 11th Exam. | 12th Exam. | 13th Exam. |
|---|---|---|---|---|---|---|---|---|---|---|---|---|---|
| Duration | 0 Months | 3 Months | 7 Months | 11 Months | | | | | | | | | |
| T-Suppressor (250–1000/mcl) | 714 | 461 | 509 | 507 | | | | | | | | | |
| T-Suppressor % (19–48%) | 51.00% | 47.00% | 46.00% | 43.00% | | | | | | | | | |
| T-Helper abs. (500–1500/mcl) | 574 | 402 | 465 | 577 | | | | | | | | | |
| T-Helper % (29–59%) | 41.00% | 41.00% | 42.00% | 49.00% | | | | | | | | | |
| Quotient (0,9–2,0) | 0.80 | 0.87 | 0.91 | 1.14 | | | | | | | | | |
| Activated T-C. abs. | | | | | | | | | | | | | |
| Activated T-C. % (2–12%) | | | | | | | | | | | | | |
| aktiv. Suppressor abs. (CD8/HLA-DR) | 112 | 78 | 89 | 130 | | | | | | | | | |
| aktiv. Suppr. % (2–12%) (CD8/HLA-D | 8.00% | 8.00% | 8.00% | 11.00% | | | | | | | | | |
| CD38 aktiv. Suppr.-T. abs. | 280 | 196 | 255 | 212 | | | | | | | | | |
| CD38 aktiv. Suppr.-T. % (5–20%) | 20.00% | 20.00% | 23.00% | 18.00% | | | | | | | | | |
| NK Cells abs. (100–600/mcl) | 84 | 59 | 66 | 71 | | | | | | | | | |
| NK Cells % (6–29%) | 6.00% | 6.00% | 6.00% | 6.00% | | | | | | | | | |
| Neopterin (<200 mcmol/mol creatinine | | | Ser. (0–10) | 8 | | | | | | | | | |
| Beta-Microglobulin (0,8–3,0 mg/l) | | 2 | 1.52 | 2 | | | | | | | | | |
| Leucocytes abs. (4,0–10,0 G/l) | 4 | 4.9 | 4.1 | 3.1 | | | | | | | | | |
| Lymphocytes % (20–40%) | 34.00% | 22.00% | 25.00% | 37.00% | | | | | | | | | |
| Eosinophiles % (1–4%) | 1.00% | 2.00% | 0.00% | 2.00% | | | | | | | | | |
| Total T-Cells (680–2750/mcl) | 1190 | 813 | 919 | 978 | | | | | | | | | |
| Total T-Cells % (60–85%) | 85.00% | 83.00% | 83.00% | 83.00% | | | | | | | | | |
| Total B-Cells (71–600/mcl) | 84 | 69 | 77 | 106 | | | | | | | | | |
| Total B-Cells % (7–23%) | 6.00% | 7.00% | 7.00% | 9.00% | | | | | | | | | |
| BSG (after 1 h; 0–8 mm) | | 14 | 11 | 14 | | | | | | | | | |
| BSG (after 2 h; 0–20 mm) | | 32 | 28 | 33 | | | | | | | | | |
| Iron (80–150 mcg/dl) | | 117 | 54 | 46 | | | | | | | | | |
| Ferritin (29–371 ng/ml) | | 15 | 10 | 8 | | | | | | | | | |
| Cholesterol (150–200 mg/dl) | | 151 | 151 | 184 | | | | | | | | | |
| HDL-Cholesterol (>50 mg/dl) | | 63 | 48 | 63 | | | | | | | | | |
| Triglycerides (70–150 mg/dl) | | 75 | 99 | 60 | | | | | | | | | |
| CIC (0,0–5,9 ng/ml) | | | 0.8 | | | | | | | | | | |
| HIV 1 p24 (pg/ml) - HIV 1 EAG | | negative | negative | | | | | | | | | | |
| Hematocrit | 37.90% | 37.20% | 36.10% | 35.80% | | | | | | | | | |

What we claim is:

1. A combination preparation comprising
   5 to 90% electrolyte-enriched plant embryos obtain by introducing germinative seeds comprising plant embryos into an electrolyte solution, and incubating said plant embryos in said electrolyte solution at a suitable temperature and for a period of time sufficient to attain an electrolyte enrichment within said plant embryos, wherein said electrolyte solution comprises; at least one of zinc, iron, potassium and magnesium ions; at least one of copper, manganese, strontium and lithium ions; and at least one of selenium, molybdenum, chromium, arsenic, vanadium, and cobalt ions and
   5 to 90% micronutrients selected from the group consisting of
   poly-unsaturated fatty acids,
   natural carotenoid mixtures,
   plant embryo extracts,
   natural anthocyano-mixtures,
   natural flavenoid mixtures,
   natural tocopherol and tocotrienol mixtures,
   vitamins and coenzymes,
   essential and non-essential amino acids and minerals.

2. A preparation as set forth in claim 1, wherein said plant embryos are at least one of wheat, oat and buckwheat embryos.

3. A preparation as set forth in claim 1, further comprising at least one vegetable concentrate.

4. A preparation as set forth in claim 3, wherein said vegetable concentrate is at least one of broccoli, parsley and cauliflower.

5. A preparation as set forth in claim 1 and having the form of capsules, chewing tablets, or powder mixtures.

6. A preparation as set forth in claim 1 packaged in a food-technologically suitable form so as to be storage-stable.

7. A preparation as set forth in claim 1 packaged in a pharmaceutical-technologically suitable form so as to be storage-stable.

8. A preparation as set forth in claim 1 in a pharmaceutical administrable form for oral administration.

9. A preparation as set forth in claim 1, wherein
   said poly-unsaturated fatty acids are a PUFA-mixture of fish oil and borage oil,
   said natural carotenoid mixtures are derived from dunaliella salina,
   said plant embryo extracts are wheat embryo extracts with octacosanole,
   said natural anthocyano-mixtures are derived from hibiscus blossoms,
   said natural flavenoid mixtures are derived from at least one of citrus fruit, tree resins or bark extracts,
   said natural tocopherol, tocotrienol mixtures are derived from wheat embryos,
   said vitamins and coenzymes are selected from the group consisting of coenzyme Q10, pyridoxole, riboflavin, folic acid, biotin, vitamin K, vitamin B 12, vitamin D3, carnitine, betain, vitamin C,
   said essential and non-essential amino acids are selected from the group consisting of N-acetyl cysteine, taurine, L-glutamine, isoleucine, leucine, lysine, methionine, phenyl alanine, threonine, tryptophae, valine, histidine, arginine, tyrosine,
   said minerals are selected from the group consisting of silica, calcium, vanadium, manganese, iron, potassium, zinc, copper, lithium, fluorine, germanium, strontium, chromium, molybdenum, selenium, iodine.

* * * * *

UNITED STATES PATENT AND TRADEMARK OFFICE
CERTIFICATE OF CORRECTION

PATENT NO. : 5,973,224

DATED : October 26, 1999

INVENTOR(S) : Norbert Fuchs, Norbert Zelch, Peter Koessler, Rupert Loidl

It is certified that error appears in the above-identified patent and that said Letters Patent is hereby corrected as shown below:

Title page, item [52], delete "800/298" and insert --514/1-- therefore.

In claim 9, column 18, line 24, after 'betain,' insert --and-- therefor.

In claim 9, column 18, line 28, delete "tryptophae" and insert --tryptophan-- therefor.

In claim 9, column 18, line 29, after 'arginine,' insert --and-- therefor.

In claim 9, column 18, line 33, after 'selenium,' insert --and-- therefor.

Signed and Sealed this

Twentieth Day of June, 2000

Q. TODD DICKINSON

*Attest:*

*Attesting Officer*  *Director of Patents and Trademarks*